(12) United States Patent
Vojnovic

(10) Patent No.: US 12,196,680 B2
(45) Date of Patent: Jan. 14, 2025

(54) METHOD FOR DETECTION OF BACTERIA IN FAECES

(71) Applicant: OXFORD OPTRONIX LTD., Abingdon (GB)

(72) Inventor: Borivoj Vojnovic, London (GB)

(73) Assignee: OXFORD OPTRONIX LTD., Abingdon (GB)

( * ) Notice: Subject to any disclaimer, the term of this patent is extended or adjusted under 35 U.S.C. 154(b) by 234 days.

(21) Appl. No.: 17/623,730

(22) PCT Filed: Jul. 6, 2020

(86) PCT No.: PCT/EP2020/069024
§ 371 (c)(1),
(2) Date: Dec. 29, 2021

(87) PCT Pub. No.: WO2021/013523
PCT Pub. Date: Jan. 28, 2021

(65) Prior Publication Data
US 2022/0252515 A1 Aug. 11, 2022

(30) Foreign Application Priority Data
Jul. 25, 2019 (GB) ..................................... 1910655

(51) Int. Cl.
*A61F 13/84* (2006.01)
*C12Q 1/04* (2006.01)
(Continued)

(52) U.S. Cl.
CPC .......... *G01N 21/6486* (2013.01); *A61F 13/84* (2013.01); *C12Q 1/04* (2013.01);
(Continued)

(58) Field of Classification Search
CPC .......... G01N 21/6486; G01N 21/6408; G01N 33/487; G01N 2201/08; A61F 13/84; A61F 2013/8473; C12Q 1/04
See application file for complete search history.

(56) References Cited

U.S. PATENT DOCUMENTS

| 5,914,247 A | 6/1999 | Casey et al. |
| 7,547,508 B1 | 6/2009 | Lefcourt et al. |
| (Continued) | | |

FOREIGN PATENT DOCUMENTS

| AU | 2008/202491 A1 | 8/2008 |
| CN | 109738366 A | 5/2019 |
| (Continued) | | |

OTHER PUBLICATIONS

International Search Report and Written Opinion for Application No. PCT/EP2020/069024, mailed on Sep. 21, 2020, 18 pages.
(Continued)

*Primary Examiner* — David P Porta
*Assistant Examiner* — Fani Polyzos Boosalis (57) ABSTRACT

A method of detecting fluorescence from bacteria suitable for determining the presence of faeces or other fluorophores, the method comprising the steps of: illuminating a target with fluorescence excitation light having an excitation wavelength and monitoring for the emission of fluorescence light from the target at wavelengths longer than the excitation wavelength.

24 Claims, 9 Drawing Sheets (51) Int. Cl.
 *G01N 21/64* (2006.01)
 *G01N 33/487* (2006.01)
(52) U.S. Cl.
 CPC ....... *G01N 21/6408* (2013.01); *G01N 33/487* (2013.01); *A61F 2013/8473* (2013.01); *G01N 2201/08* (2013.01)

(56) References Cited

U.S. PATENT DOCUMENTS

| | | | |
|---|---|---|---|
| 11,850,118 B2 * | 12/2023 | Schiffer | ............ G01N 21/6428 |
| 2003/0160182 A1 | 8/2003 | Petrich et al. | |
| 2006/0008866 A1 | 1/2006 | Flick et al. | |
| 2015/0282993 A1 | 10/2015 | Lin | |
| 2017/0002394 A1 | 1/2017 | Choi et al. | |

FOREIGN PATENT DOCUMENTS

| | | | | |
|---|---|---|---|---|
| EP | 2926786 A1 | 10/2015 | | |
| EP | 3117203 B1 * | 2/2021 | ............... C12Q 1/04 | |
| JP | H04-30406 U | 3/1992 | | |
| JP | 2001161394 A | 6/2001 | | |
| JP | 2001269364 A | 10/2001 | | |
| JP | 2005224411 A | 8/2005 | | |
| JP | 2011-521237 A | 7/2011 | | |
| JP | 2016-519655 A | 7/2016 | | |
| KR | 20180085579 A | 7/2018 | | |
| WO | WO-2007064841 A2 * | 6/2007 | ........... G01N 21/643 | |
| WO | 2009/140757 A1 | 11/2009 | | |
| WO | 2013/180583 A1 | 12/2013 | | |
| WO | 2015/137828 A1 | 9/2015 | | |

OTHER PUBLICATIONS

Combined Search and Examination report for Application No. GB1910655.8, mailed on Dec. 2, 2019, 10 pages.
International Preliminary Report on Patentability for Application No. PCT/EP2020/069024, mailed on Feb. 3, 2022, 11 pages.
Giana et al., "Rapid Identification of Bacterial Species by Fluorescence Spectroscopy and Classification Through Principal Components Analysis", Journal of Fluorescence, Nov. 2003, vol. 13, No. 6, pp. 489-493.

* cited by examiner

METHOD FOR DETECTION OF BACTERIA IN FAECES

CROSS-REFERENCE TO RELATED APPLICATIONS

This application is a National Phase Application of International Patent Application No. PCT/EP2020/069024, filed on Jul. 6, 2020, which is based on and claims priority to and benefits of British Patent Application GB 1910655.8, entitled "METHOD FOR DETECTION OF BACTERIA IN FAECES" and filed on Jul. 25, 2019. The entire content of all of the above identified applications is incorporated herein by reference.

FIELD OF THE INVENTION

The present invention relates to a method of detecting fluorescence from bacteria, and in particular, to detecting fluorescence of bacteria in an incontinence pad, diaper or nappy, an fibre optic cable or other form of light guide for use in the method, and an apparatus for performing the method of the invention.

BACKGROUND TO THE INVENTION

Faecal incontinence (inability to control the bowels) is a devastating social and hygiene problem, affecting 2-3% of adults. There is a particularly high prevalence among frail older people in care homes (nursing facilities) or in hospital environments. People with either blunted sensation (e.g. neurological conditions) or diminished awareness (e.g. dementia) often do not know if they have passed stool (faeces) accidentally into an incontinence pad, or cannot distinguish between passing stool or flatus and so may repeatedly visit the toilet unnecessarily. This can be burdensome for some, for example patients who are wheelchair-bound and must find an accessible toilet, transfer and remove clothing and incontinence pads. Carers, whether in a hospital, care home, or in the person's own home, likewise often need to check, but there is no practical way to do this without removing clothing, which can be challenging if it involves a frail person.

Existing urinary incontinence products incorporate a hydrophobic layer and are designed specifically to absorb and contain urine. They cannot, however, absorb stool. Modern stay-dry surfaces and super-absorbent pads can accommodate large volumes of urine without damaging vulnerable skin or creating an unpleasant odour. Therefore, if only urine has been passed in a pad, changing can be delayed until the capacity of the pad is approached. However, once stool is passed the product needs immediate changing and the skin must be washed as soon as possible to prevent skin damage. There is thus a need for prompt and accurate signalling when a patient has passed stool.

SUMMARY OF THE INVENTION

According to a first aspect of the invention, there is provided a method of detecting fluorescence from bacteria suitable for determining the presence of faeces or other fluorophores, the method comprising the steps of: illuminating a target with excitation light having an excitation wavelength and monitoring for the emission of fluorescence light from the target at wavelengths longer than the excitation wavelength.

The wavelength of the excitation light may be in the range of 420 nm to 645 nm, and more particularly the wavelength of the excitation light may have a central wavelength of substantially 635 nm. The fluorescence light may have a wavelength of 650 nm or larger. The excitation wavelength may comprise a plurality of wavelengths corresponding to one or more porphyrin Q-bands.

The target may be a container for receiving bodily fluids or bodily excrement, and more specifically the container may be an incontinence pad, diaper or nappy or a container for receiving a sample of bodily fluid or bodily excrement in vitro.

The method according to the first aspect may further comprise modulating the intensity or frequency of the excitation light, and optionally detecting a corresponding modulation in light emitted by the target; and filtering out emitted light without said modulation. The method may further comprise detecting a fluorescence lifetime associated with sample fluorescence, the lifetime being detected using a time-resolved or phase resolved detection approach.

The method may further comprise providing a light source and coupling light output from said light source into a light guide, wherein said illuminating is carried out by light emitted from the light guide, and wherein optionally the light guide is an optical fibre. The step of monitoring may comprise monitoring for light coupled from the target into the light guide at said wavelength larger than the wavelength of the excitation light.

The light source and/or a detector may be provided in an incontinence pad, diaper or nappy.

The method may further comprise measuring the fluorescence light emission and comparing the emission to a predetermined threshold value. The method may further comprise detecting the wavelength spectrum and/or the fluorescence lifetime of the fluorescence light.

Optionally, a signal is generated to notify a user of the presence of bacteria.

According to a second aspect of the invention there is provided a detection system for detecting the presence of faeces, the system comprising: a light source; a source optical fibre, wherein the source optical fibre is optically coupled to the light source; a receiver optical fibre; a detector, wherein the detector is optically coupled to the receiver optical fibre.

The source optical fibre and the receiver optical fibre may be the same or optical fibre, or may be different optical fibres. The source optical fibre may be a fibre-optic cable comprising a core and a cladding, wherein the cladding may comprise a plurality of discontinuous portions providing an optical path for light to be coupled into or out of the fibre. The discontinuous portions may be arranged in a non-linear pattern in which adjacent gaps are positioned increasingly far apart from one another in order to maintain a constant degree of light leakage along the cable.

The source optical fibre and the receiver optical fibre may be the same optical fibre, and the optical fibre may be optically coupled to the detector and to the light source, and the detector and light source may be coupled to the optical fibre at the same end of the optical fibre or at opposite ends of the optical fibre.

The system may further comprise a pad, wherein the source optical fibre and/or the receiver optical fibre are attached to the pad or integrally formed with the pad. The system may further comprise a communication module for sending and/or receiving data to or from one or more external devices. The system may further comprise an alarm, wherein the alarm is one of an optical alarm, an acoustic alarm or a tactile alarm.

BRIEF DESCRIPTION OF THE FIGURES

Some embodiments of the invention will now be described by way of example only and with reference to the accompanying drawings, in which.

DETAILED DESCRIPTION

Herein disclosed is a method and system for detecting bacteria present in stool. The problem of detecting the presence of stool can be addressed by exploiting the fact that certain bacteria which are prevalent in faeces have characteristic fluorescence properties. Normal faeces contain a very large number of bacteria and 25-54% of their mass is bacterial biomass.

Fluorescence from faeces appears to originate from protoporphyrin IX, coproporphyrin and conversion to pemptoporphyrin and deuteroporphyrin but is not limited to these moieties.

Fluorescing species, such as porphyrins, usually exhibit a large Stokes shift. The presence of porphyrins, and thus of bacteria, can therefore be detected by exciting the porphyrins with light at a given wavelength band ("excitation light"), and monitoring for fluorescence emissions ("fluorescence light") at longer wavelengths than the wavelength of the excitation light.

The absorption (excitation) spectra of porphyrins exhibit a strong so-called "Soret band" in the blue region of the visible spectrum, as illustrated with reference number 1 in FIG. 1. This intense Soret band is attributed to the S0 to S2 electronic states/energy transitions. The location of this band will have the absorption maximum below 430 nm, typically in the range of 400-420 nm.

The absorption spectrum of porphyrins is however not restricted to the Soret band: there are other, weaker, absorption bands called 'Q-bands', illustrated with reference number 2 in FIG. 1. In porphyrins, the Q-bands are split due to vibrational excitations, whereby two bands are produced due to transition from ground state to two vibrational states of the excited state (Q(0,0) and Q(1,0)). Furthermore, the presence of the NH protons breaks the symmetry and as a result these bands are further split into two bands each. Therefore, four Q-bands (Qx(0,0), Qy(0,0), Qx(1,0) and Qy(1,0)) can be observed. Thus, excitation of porphyrins at peak absorbance wavelengths corresponding to the peaks of the Soret band or of the Q-bands is possible.

Figure 1:
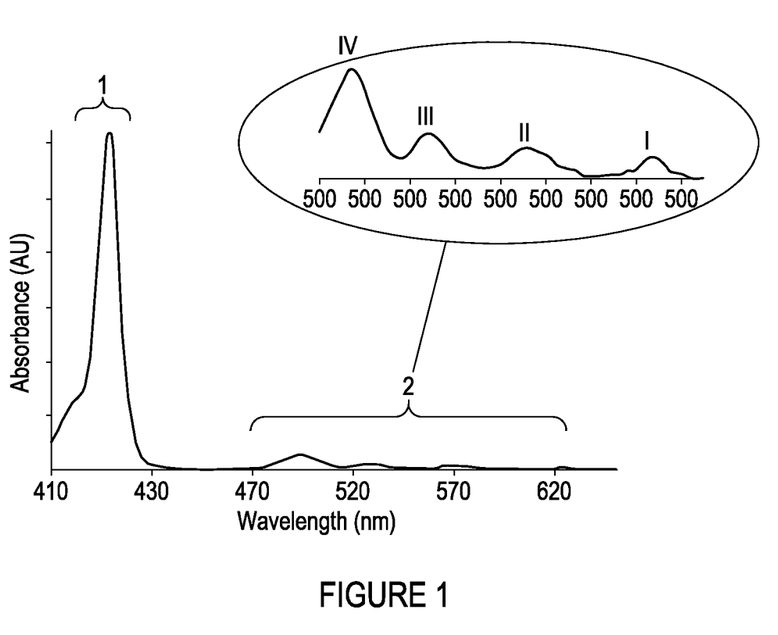
FIG. 1 illustrates a typical porphyrin excitation spectrum, exhibiting a strong Soret excitation band and a plurality of weaker Q-bands.

Typically, the four porphyrin Q-bands will have absorption peaks at about 505 nm ("Q-IV"), about 535 nm ("Q-III"), about 575 nm ("Q-II") and about 635 nm ("Q-I"), as shown in FIG. 1. The excitation light may be chosen to have a wavelength corresponding substantially to a peak absorption wavelength of a porphyrin Q-IV band, Q-III band, Q-II band, Q-I band. By "corresponding substantially" is meant that the excitation light may have an optimum wavelength in a range of ±10 nm, preferably ±5 nm relative to the peak absorption wavelength of the respective Q-band. The width of the excitation spectrum may be smaller or larger than the width of the illustrated absorption peaks.

By using excitation light having a wavelength in the range of about 500 to 645 nm, one or more of the Q-bands of bacterial porphyrins can be excited, leading to the production of fluorescence emission. Alternatively, due to the strong Soret band absorption, porphyrins can be excited using irradiation in the blue or UV region of the spectrum, for example at about 415-420 nm or below about 400 nm. The use of such excitation wavelengths leads to correspondingly strong fluorescence emissions and therefore allows for the straightforward detection of the presence of bacteria. If excitation is performed in the porphyrin Soret band, e.g. using a wavelength of about 430 nm or below, fluorescence emission is typically observed at about 650 nm or above.

Soret band excitation wavelengths could be used for the detection of faecal matter, for example, in an incontinence pad. However, prolonged or long-term exposure to light in the blue and/or UV regions of the spectrum is considered potentially toxic to skin and other tissues. Though such wavelengths are not readily absorbed by DNA they can induce DNA damage indirectly through other cellular structures with formation of reactive oxygen species that can transfer the photon energy to DNA via mutagenic oxidative intermediates such as 8-hydroxydeoxyguanosine (8-OHdG). The detection method therefore preferably avoids the prolonged use of such wavelengths.

Furthermore, traces of grease on the skin (creams, ointments etc.), and optical whiteners (as found in some makes of incontinence pads and nappies) can also fluoresce under blue light or UV light. Therefore, if fluorescence detection is performed using Soret band excitation light in an incontinence pad or nappy, a false-positive detection of bacteria is likely.

Figure 2:
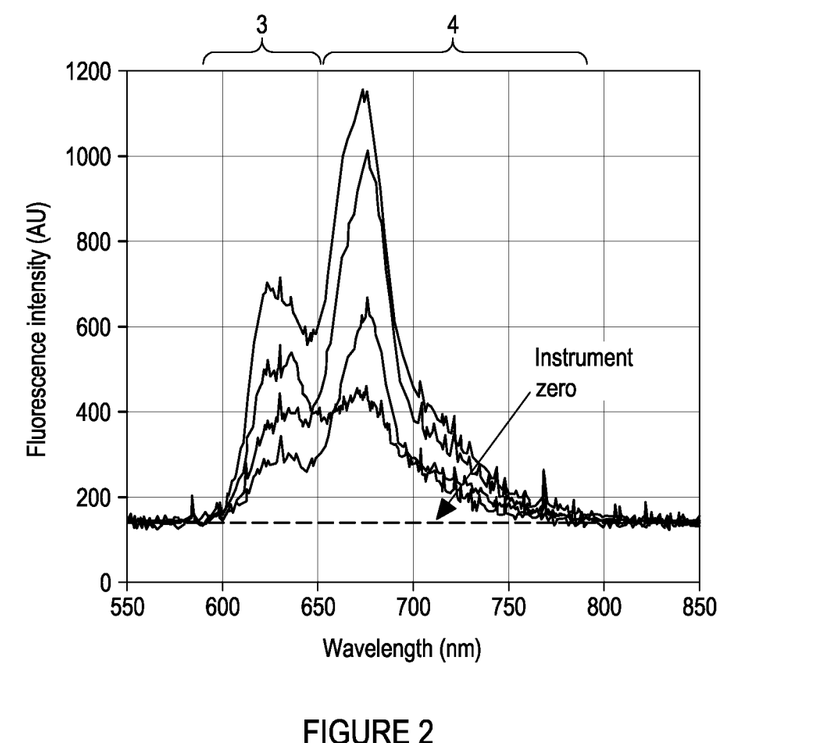
FIG. 2 is a graph of spectral measurements of fluorescence emissions from several faecal samples.

The inventors have realised that Q-band excitation light (i.e. excitation light having a wavelength of 500 to 645 nm) can however be used safely. FIG. 2 shows spectra obtained from several faecal samples illuminated with light in the 500 to 645 nm range, as illustrated with reference number 3. As shown in FIG. 2, the resulting Stokes shift leads to fluorescence at a wavelength of about 650 nm or above. The emission spectra will display principal emission peaks from about 675 nm and to about 735 nm. These wavelengths depend on porphyrin species as well as the excitation wavelength employed.

There are other advantages to employing longer wavelength Q-band excitation light for the purpose of detecting the presence of stool. Stool samples can be optically dense, particularly if they are large in volume. This can lead to significant self-absorption (inner-filter effect). Rayleigh scattering of the excitation and fluorescence emission light is inversely proportional to the $4^{th}$ power of wavelength and Mie scattering also reduces as the wavelength is increased. These effects can increase the intensity of fluorescence emission light which can be detected, making detection easier. Longer wavelengths of excitation light show a greatly-reduced extent of self-absorption and allow a greater depth of sample to be illuminated, thus leading to improved detection.

There are thus particular advantages to exciting the Q-I or Q-II bands over exciting the Q-III or Q-IV bands, despite weaker absorption in the longer-wavelength Q-bands.

In the present method, therefore, the detection of bacteria may be performed by illuminating a target with excitation light having a wavelength in the range 500 nm to 645 nm and simultaneously monitoring for the presence of fluorescence light having a wavelength of 650 nm or greater. The target may be a soiled incontinence pad, diaper, nappy worn by a user. Alternatively, the target may be a sample of bodily fluid in vitro, or other sample suspected of containing bacteria.

Certain bacteria associated with urinary infections may also contain porphyrins and therefore undergo similar fluorescence processes as outlined above. Therefore, when the target to be illuminated is an incontinence pad, diaper or nappy as described above, the detection of bacteria therefore may also correspond to the detection of urine associated with a urinary infection.

Where the illumination target is an incontinence pad, diaper or nappy the detection of bacteria is preferably performed while a user is wearing said incontinence pad, diaper or nappy.

In order to separate the excitation light from the fluorescence emission and therefore ensure that only the genuine fluorescence emission is detected, a variety of methods can be used. For instance, fluorescence signals can be detected with an optical detector or with a spectrometer. Alternatively, fluorescence lifetime information can be extracted, using frequency-modulated or pulsed excitations followed by fluorescence phase or lifetime detection, respectively. In most cases, it is desirable to separate the fluorescence emissions form the excitation light using one or more filters.

Excitation light having a wavelength corresponding substantially to a peak absorption wavelength of a porphyrin Q-I band, (e.g. 635±10 nm and particularly 635±5 nm) provides excellent performance in detection ability, emission efficiency, minimised scattering and low cost of light sources and detectors.

The conversion of the collected fluorescence light into a meaningful output is usually required. This conversion step may include determination the fluorescence emission by a variety of detection approaches, and comparing it to a predetermined threshold value. If the level of fluorescence is above a threshold value, then a positive identification may be made signifying the presence of bacteria and thus of stool.

Where fluorescence is detected, the method may further comprise generating a signal to notify a user of the presence of bacteria (e.g. to notify a user of the presence of stool). The signal may for example be a sound or a visual indication (e.g. a light or a message on a screen such as a screen of a computer or handheld device).

Figure 3:
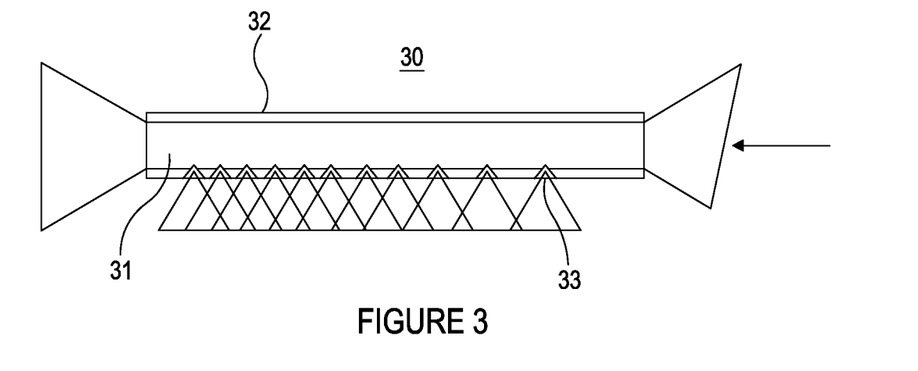
FIG. 3 illustrates an example 'leaky' light guide.

Illuminating a target with excitation light and collecting the fluorescence emission may comprise transmitting the excitation light along a light guide to the target. In the vicinity of the target, the light guide is made intentionally "leaky". FIG. 3 shows an example fibre optic cable 30 operating as a light guide suitable for illuminating a target. The fibre optic cable 30 comprises a core 31 having a refractive index n1 and a cladding 32 having a refractive index n2 wherein n2<n1. The core 30 and cladding 32 may be of any material known in the art for fibre optic cables, e.g. silica, glass or polymers or other forms of light guide.

Where the target is an incontinence pad, diaper or nappy it is desirable to illuminate a plurality of locations within the target in order to optimise detection of bacteria. In order to illuminate the target area, various means can be used to distribute the excitation light over a large area, and collect fluorescence emissions from said area. Several approaches use "leaky" fibre optic cables. The cladding 32 comprises a plurality of discontinuous portions 33. These discontinuous portions 33 ("gaps" or "discontinuities") in the cladding 32 expose the core 31. In such a "leaky" cable, excitation light can "leak" out of the core 31 via the gaps 33 in the cladding 32, thereby illuminating a plurality of locations within the target which are adjacent to the gaps 33. Fluorescence light arising from any bacteria present at such locations can also enter the fibre-optic cable via the gaps 33 in the cladding (i.e. it is "collected" by the cable).

By providing a plurality of discontinuous portions 33 along the length of the fibre optic cable 30, or other type of light guide, total internal reflectance of light carried by the fibre optic cable 30 is partially suppressed in these portions and light leaches out across a length of the fibre optic cable 30. Compared to a fibre optic cable having a single "open" end, this increases the area over which the fibre optic cable 30 can detect the presence of bacteria in a target, e.g. in faecal matter in a pad. The gaps 33 may extend around the whole or part of the circumference of the fibre optic cable 30. The gaps 33 may take the form of pinpricks, slits, scratches or notches in the cladding and they may extend around the circumference of the fibre optic cable 30 or extend around only a portion thereof. The gap 33 may be one or more helical cuts along the length of the fibre optic cable 30. The gaps 33 may be formed by scoring, etching, laser-cutting, piercing, sanding, sand-blasting, or any other suitable technique.

The gaps 33 in the fibre cladding 32 may be positioned and sized such that light leakage out of the core 31 is substantially uniform at each gap. This also ensures that a substantially uniform amount of fluorescence light is collected per unit length (e.g. per mm or per cm) by the optical fibre. This can be achieved by arranging similar gaps 33 in a non-linear pattern in which adjacent gaps 33 are positioned increasingly closer from one another towards the distal end of the fibre optic in order to maintain a constant degree of light leakage, as shown in FIG. 3.

In adult pads or nappies the target area may cover a length of up to 10-15 cm and a width of typically of 5-10 cm. In diapers or nappies for infants this length may be reduced accordingly.

Light exiting the fibre optic cable 30 will be scattered upon encountering the material of the target, such as the material of the incontinence pad, diaper or nappy. In this way, the portion of the target which is illuminated increases beyond only the portion immediately adjacent to the gap 33 in the cladding 32. Preferably, the fibre optic cable 30 has a diameter of less than 1 mm, such as 0.75 mm±0.25 mm or less, although other readily available fibre optic cables 30 are readily available and are particularly suitable for uses described herein.

The fibre optic cable can be made 'leaky' in other ways. For instance, the cable may be bent to form numerous curves, for example in a wave-like shape. A curve will increase the angle of incidence of light travelling within the fibre onto the interface between the core and the cladding, which will decrease the amount of internal reflection. When the fibre is woven into the material, a plurality of curves can be included to create a corresponding plurality of areas where the emission and absorption light can be coupled into the fibre or out of the fibre.

Instead of a single fibre optic cable, a plurality of cables could be used. The cables may be arranged in the form of a fibre bundle or may be parallel to or at an angle (e.g. perpendicular to) one another. In such cases, the technical difficulties of manufacturing multiple fibres would be rewarded by having a significantly thinner sensor which is potentially of acceptable sensitivity even when using less efficient fibres and increasing further the sensed area. When woven into the fabric of a pad, the fibres could also be arranged in a mesh-type arrangement with respect to each other.

Figure 4A:
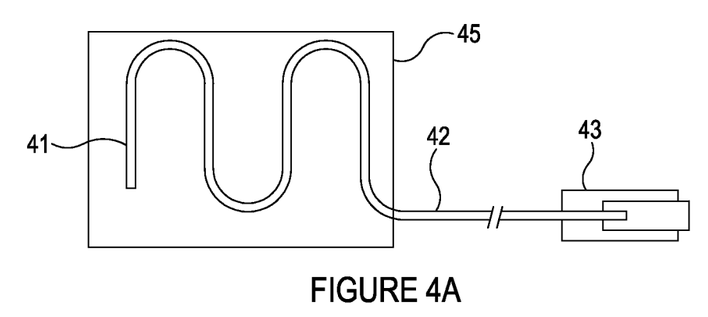
FIGS. 4A-4C illustrate schematically several arrangements of leaky optical fibres in a target sensing area.
Figure 4B:
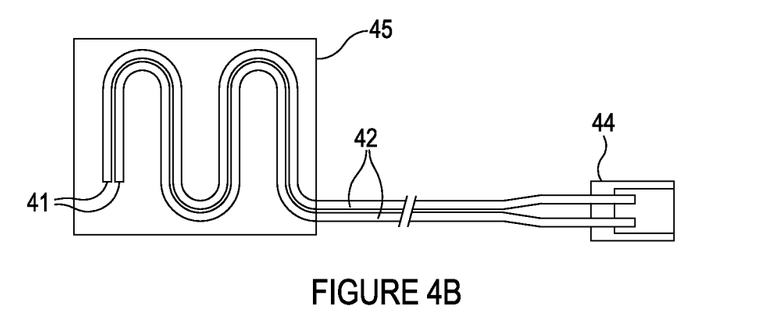
Figure 4C:
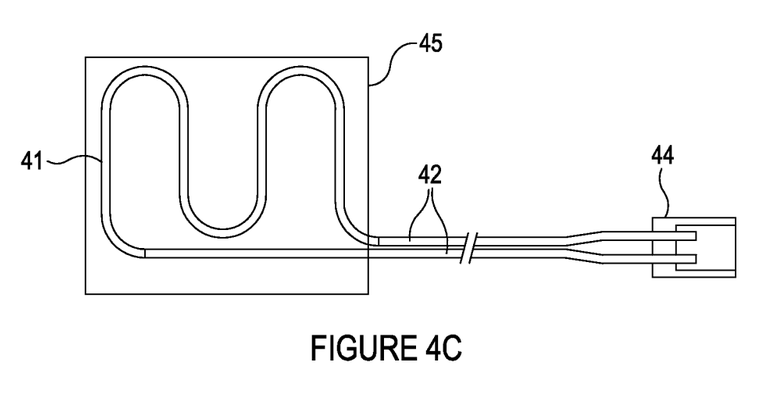

Depending on the optical arrangements used to deliver excitation light and to collect fluorescence emission light, one or more leaky fibres can be used and can be arranged in numerous arrangements as shown in FIGS. 4A-4C. When a single fibre is used, as shown in FIG. 4A, fibre 42 operates as a conventional light guide, but is made leaky in portions 41 and terminates in connector 43. The leaky portions meander across the target area 45 where faecal matter is expected to be present.

An alternative arrangement is presented in FIG. 4B. Here two fibres 42 are made leaky in portions 41 and are terminated in a dual fibre connector 44. The fibres are placed adjacent to each other and one of the fibres transmits excitation light while the other collects fluorescence emission light. The leaky portions 41 meander across the target area 45. The leaky portions of the fibre optic cables must be sufficiently close to each other such that the two cables can illuminate/receive light from the target 45, and interact with the same sensing area.

An alternative approach is presented in FIG. 4C. This again uses a dual fibre connector 44, but this terminates two ends of a single optical fibre. This fibre has leaky portions 41 with non-leaky portions 42. The fibre thus provides excitation light over the target area and collects fluorescence emission from the target area 45.

The meandering portions of the fibres 41 in FIGS. 4A-4C may be attached to a highly porous and flexible substrate that allows passage of urine to underlying absorbent areas of the pad. The leaky portions may run parallel to each other, and may be tied, glued, woven into a sensor pad or otherwise affixed in place.

Figure 5:
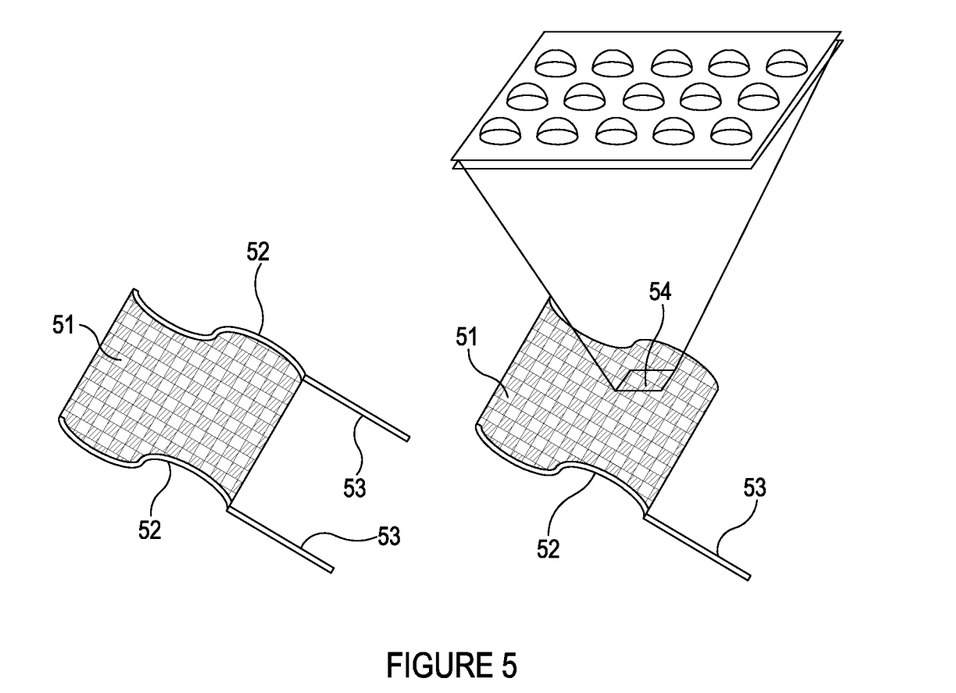
FIG. 5 illustrates schematically arrangements that employ engineered diffusers placed in a target sensing area.

Yet other approaches are illustrated in FIG. 5. Here, non-leaky fibre(s) 53 are used to transmit excitation light and collect fluorescence emission to and from leaky fibres 52 and a flexible diffuser 51 similar to those used in LED backlight panels. Such engineered diffusers can be made out of flexible PDMS/PMMA. These or other forms of light guide plates can be connected with one or more fibre optic cables to a detection unit. In this instance, the fibres 52 are made leaky only where they are in contact with the flexible diffuser 51. Other similar approaches for distributing light over a large area are also suitable. The diffuser 51 acts as a large light guide operating though total internal reflection. The total internal reflection is disrupted at intervals by the incorporation of dips or bumps, as shown in the expanded portion 54, across the sheet to form a side-illuminated diffuser. This can thus also act as a collector of light across a large target area. Numerous holes must be present in the diffuser 51 to allow passage of urine.

Alternatively, the light sources and detectors may be placed close to the target area and signal information taken to a signal processing unit by electrical rather than by optical means. The simplicity of using electrical rather than optical connections is balanced by the challenges of developing ultra-thin, flexible optical filters to remove the excitation light form the detected signal.

The fibre optic cable (or cables) described above may form part of a fluorescence detection system, comprising one or more light guides, a light source and an optical detector. Further details regarding these components (and other optional components) are set out below.

The light source and detector are typically incorporated into a unit which can be selectively connected to the fibre light delivery and sensing cable(s). The light source may be coherent or incoherent, may operate continuously during the sensing periods, may be modulated or may be pulsed.

A red (630-640 nm) laser light source may be preferable. Such a source combines the conflicting requirements of low cost, low optical étendue (a term of the art indicating the ability to focus the beam, the product of source area and solid angle emitted by the source) and low operating power, all of which are essential for long term, reliable operation. The brightness and low étendue allows straightforward light launching in the fibre. In particular, a wavelength of 635 nm may be employed.

Optionally, the light source's output power can be sensed by a photodiode internal to the light source (e.g. laser) in order to maintain the average output power at a user-defined value. Optionally temperature control of the light source may be required in order to stabilise emission wavelength. Optionally, the light source is only switched on intermittently to save power, for example a short pulse every 10 seconds, or 30 seconds or every minute, or any other convenient time period.

The detector may be a photodiode or an avalanche photodiode. Silicon photodiodes or silicon avalanche photodiodes are particularly suitable due to their high optical-electrical quantum efficiency and responsivity, which are particularly good in wavelength ranges corresponding to the fluorescence wavelengths associated with Q-band excitation of porphyrins.

Alternatively the detector may be a spectrometer or a time-resolved detector, e.g. a single-photon avalanche diode (SPAD). Numerous fluorescence detection approaches known to those skilled in the art of fluorescence detection may be used.

The light delivery and sensing fibre optic cable(s) are typically disposable because they will be contaminated whereas the unit containing the light source and detector, along with other signal processing electronics is reusable. The disposable parts are intended for single use and the costs for those parts are preferably minimised.

The fluorescence emission detector may be configured to only detect light in a range of wavelengths corresponding to the fluorescence emission band to be detected, and not the excitation wavelength(s).

Figure 6A:
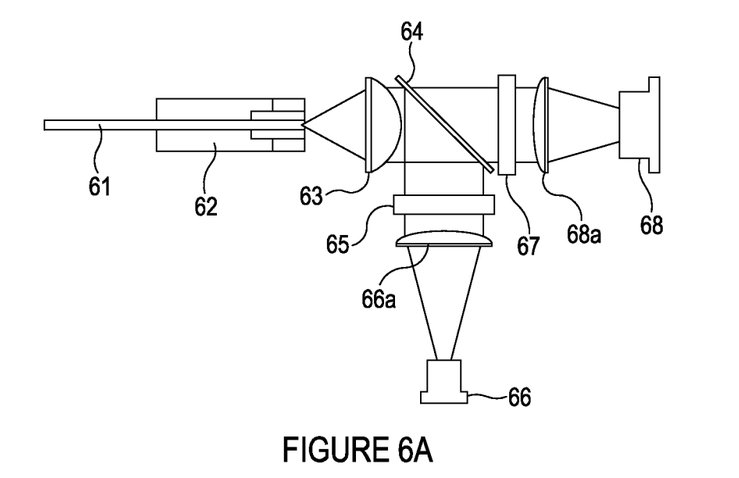
FIGS. 6A-6B illustrate examples of coupling and detecting fluorescence light into and from a single detection fibre.
Figure 6B:
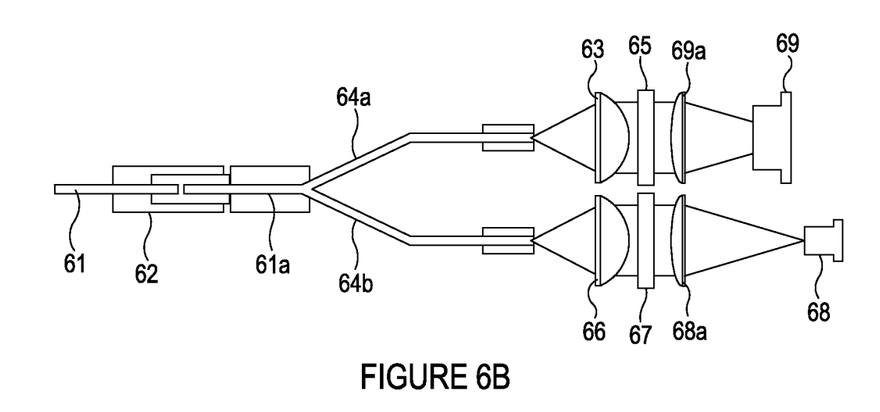

The arrangement shown in FIG. 4A may be coupled to exemplary fluorescence excitation and detection system as shown in FIG. 6A or 6B. A conventional fluorescence detection system, based on a long-pass dichromatic reflector 64 is shown in FIG. 6A. A single fibre 61 is connected to the fluorescence detection system via connector 62 and its output is collimated by lens 63. The collimated fluorescence output is transmitted by dichromatic filter 64 onto a detector 68 via a long pass or notch filter 67. The detector 68 may require the use of a focusing lens 68a.

The dichromatic reflector 64 reflects excitation light from source 66. This light may require a collimating lens 66a and a low pass filter 65 to remove longer wavelength emission sidebands from the fluorescence excitation source 66. The collimated fluorescence excitation light is focused onto fibre 61 with lens 63.

Alternatively, short pass dichromatic reflectors 65 may be used and the positions of the detector 68 and its filter 67 and lens 68a transposed with the source 66, its collimating lens 66a and the sideband rejection filter 65. The angle between the excitation and emission light axes need not be 90 degrees but could be any angle defined by the design of dichromatic reflector 64.

Alternatively, the dichromatic reflector may be replaced with a 50:50 beam splitter cube or plate. In this case approximately 50% of the excitation light will be lost, as will 50% of the emission light. However, operation at close Stokes shifts is then possible, since dichromatic reflectors with a sharp transition between transmitted and reflected wavelengths are difficult to manufacture.

An arrangement that provides a similar level of loss and that removes the need for a dichromatic reflector altogether is shown is FIG. 6B. Here, light from source 68 that may require collimation by lens 68a is filtered by a short pass filter 67 onto an optical fibre 64b by lens 66. Fibre 64b is part of a fibre splitter/combiner arrangement with three ports 64a, 64b and 61a. Approximately 50% of light entering fibre 64b is transmitted to port 61a. Similarly approximately 50% of the fluorescence light emission present in port 61a is present at the output of port 64a. This light is collimated by lens 63 and passed through a long pass filter 65 onto a detector 69 that may also require a focusing lens 69a. As before, the filter removes excitation light from reaching the detector 69.

In the exemplary systems presented in FIGS. 6A and 6B, the excitation light and the emission light are carried to the target area by a single fibre. The connector 62 may allow free rotation of the cable. Preferably, the connector employs rotational and axial latching.

Although conventional lenses and filters are shown in FIGS. 6A and 6B, a range of other optical components, such as gradient index lenses, Fabry-Perot filters and other all-fibre components may be used.

Figure 7:
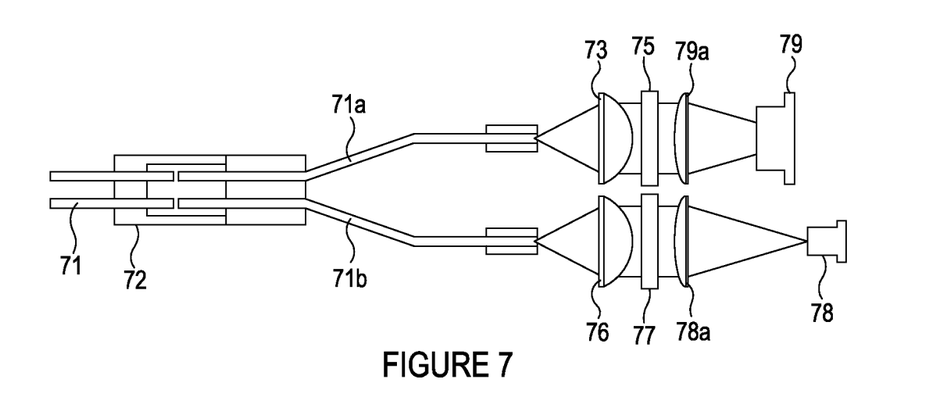
FIG. 7 illustrates an example of coupling and detecting fluorescence light into and from two fibres used for fluorescence detection.

An exemplary fluorescence excitation and fluorescence detection system with dual fibre ports, as required by the arrangements presented in FIGS. 4B and 4C is presented in FIG. 7.

Excitation light from source 78, associated collimating lens 78a, and sideband rejection filter 77 is focused by lens 76 onto excitation light fibre 71b used to connect to a dual fibre connector 72. Similarly light from fluorescence emission light fibre 71a is collimated by lens 73, and any excitation light present is removed by a long pass or notch filter 75. The thus filtered light is focused by lens 79a onto detector 79.

In this exemplary system the connector 72 must not allow free rotation of the cable. Preferably, the connector employs an axial latching mechanism.

Although steady-state excitation and detection are simplest to use, operating continuously or in short bursts, other detection approaches are also possible in the exemplary arrangements shown in FIGS. 6A-6B and 7. These include the use of a spectrometer to replace the detector, wherein the spectrometer may detect a wavelength emission spectrum of the emitted light. Alternatively, fluorescence lifetime measurement approaches may be employed, where the light source output is pulsed or modulated at one or more frequencies appropriate for the fluorescence lifetime of the sample. The detector can then be a time-resolved detector or a phase-demodulated detector. Spectral information can be useful in discriminating the spectral peaks (as shown in FIG. 2), with dispersion information potentially providing insight into other aspects of patient health. Likewise, time-resolved information can provide similar information, while having the further advantage of being insensitive to attenuation changes in the optical fibres. Any suitable optical arrangements known to those skilled in the art may be used.

When the level of the processed detected fluorescence information exceeds a pre-determined threshold, a positive identification of bacteria (e.g. in faecal matter) is made. Preferably this is accompanied by sending an alert to a user (e.g. the wearer of an incontinence pad comprising the light guidance arrangements shown in FIGS. 4 and 5, or to a carer such as a nurse or doctor). Where the detection is performed in order to detect the presence of stool, this alert may then prompt the change of a soiled incontinence pad/diaper for a clean one.

The bacterial detection system may further comprise a signal processing unit. The signal processing unit receives electronic signals from the detector and processes them to determine whether the optical detector has detected fluorescence information of interest above a predetermined threshold value. A predetermined threshold value may be set in order to eliminate "false positive" detection of bacteria arising from unavoidable background noise such as fluorescence intrinsically generated by any of the optical components of the apparatus or from other light sources.

The detection of bacteria may be performed continuously (i.e. by continually generating excitation light and monitoring for fluorescence light) or may be performed at discrete intervals of time separated by periods where no detection is performed. Detection at discrete intervals of time may help to conserve power (leading to longer device lifetime where, for example, the device is battery-powered). In addition, particularly in the case of stool detection, continuous monitoring may be unnecessary due to the low frequency with which stool is passed by a patient. Therefore, detection may be performed at regular intervals, for example at intervals of 20 minutes or less, preferably 5-15 minutes. When detection is performed, this need only be performed for long enough to enable the detection of the presence or absence of fluorescence. Thus, during each detection interval, excitation light is preferably provided for a few seconds or less.

The excitation light may be modulated and the signal processing unit can be configured to detect only the corresponding modulation in the fluorescence light. The intensity and/or frequency of the excitation light may be modulated. Such synchronous detection approaches are known to those skilled in the art of signal processing. Light sources not associated with the excitation/emission process, such as ambient light, will not be modulated in the same way, and therefore may be filtered out. The modulation waveforms can be of sinusoidal or square shapes, or of other shapes known to those skilled in the art of synchronous demodulation.

The fluorescence detection system described above may be integrated into an incontinence pad, diaper or nappy. Pads, diapers and nappies are well known in the art and their exact construction is not essential for the working the invention. However, they generally include an elongate absorbent portion, which commonly includes an anti-odorant. In the following discussion the term "pad" will be used for brevity but should be understood as encompassing not only incontinence pads but also diapers and nappies. A pad can also refer to a separate insert with the leaky optical fibre(s) or other light diffusive arrangements, whereby the pad is inserted into a diaper, such that the diaper design does not need to be changed.

The distributed sensing arrangements as described above may be integrally formed within the pad (i.e. both cable and pad being disposable as a unit), or the fibre optic cable(s) may be removable from the pad, in which case the fibre optic cable can be sterilised after use and re-used.

The pad may include means for positioning the distributed sensing arrangement, especially the portion of the cable containing the plurality of discontinuous portions, substantially centrally within the pad. As used herein, the term "centrally" is to be understood as central with respect to the longer dimension of the pad (i.e. as for the longer dimension of the pad, the cable runs front to back relative to the user of the pad). A central arrangement of the sensor provides a more reliable method of detecting bacteria because soiling (e.g. by faeces, urine or other discharge) usually occurs centrally within the pad. Central location may be achieved, for instance, by the presence of a sleeve for holding the cable in place, or by loops of material through which the cable can be fed. In certain embodiments the cable may be woven into the fabric of the pad.

It will be appreciated that the light source, the detector and additional processing systems require a power source. The power source may be integral within the detection system (i.e. a cell or battery). Alternatively (e.g. in a clinical setting), the system may include means of connection to an external low voltage power source (e.g. through the power connections of a USB connector), also used for charging the cell or battery.

The fluorescence detection system may comprise a compact housing, for containing the reusable components (light source, detector, communication module, signal processing unit etc.). This housing could fit in the pocket of a nappy or similar. The housing may have an aperture therein defining an optical port, as outlined below.

The housing may comprise means for resetting the system once the incontinence pad has been replaced, such as a push button or switch. Alternatively, the system may be reset through external data links, as described below. The housing may further comprise an indicator, configured to alert a user when a positive identification of bacteria has been made. The indicator may be a visible light, sounder, buzzer. When the fluorescence detection system is worn by e.g. wheelchair bound users, a vibrating alert system may be preferred.

The fluorescence detection system may further comprise an optical port for receiving an end of the connecting fibre(s). The connecting fibre(s) may further comprise a magnetic portion at one end, configured to magnetically latch onto a magnet on or in the port. As such, the connecting fibre(s) can be selectively attached to the optical port (e.g. plugged/unplugged), allowing the leaky fibre optic cable to be integrally formed into a disposable portion (such as an incontinence pad, nappy, or a disposable test probe), while the remaining components in the housing can be reused.

Figure 8:
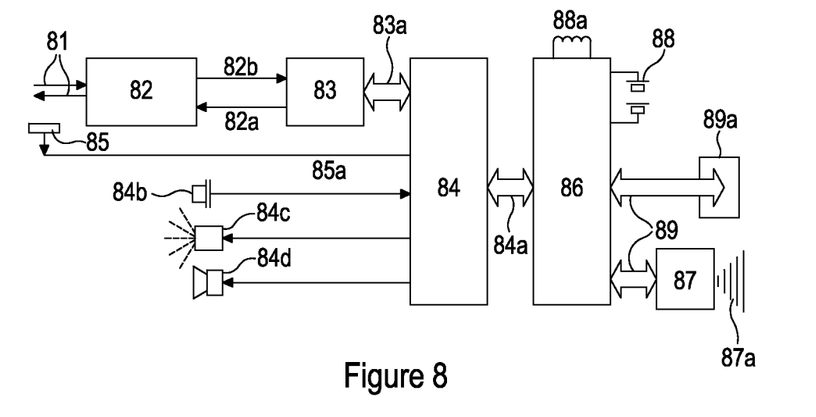
FIG. 8 illustrates a block diagram for processing optical signals in a fluorescence detection system as shown in any of FIGS. 4 to 7.

The optical port may further comprise a sensor 85 for detecting whether the connecting fibre(s) is properly inserted into the port, or if it has become disconnected. The sensor 85 may be configured to send this 'fibre-connected/disconnected' signal to a processing and communications units, as shown in FIG. 8 and as set out below. Alternatively, the sensing of the cable may be performed by sensing reflections from an open connector.

FIG. 8 includes optical paths 81 (or electrical connections when the light sources and detectors are placed within the pad) connected to an optical detection subsystem 82, such as the systems or arrangements described in connection with any of FIGS. 4 to 7. The optical detection subsystem 82 provides electrical signals 82a and 82b, which correspond to fluorescence excitation and emission signals, respectively. These signals are processed by electronic amplifiers, filters and/or drive circuits 83 using designs well known to those skilled in the art of processing electrical signals, and used to drive optical sources and electrical signals from opto-electronic devices, using synchronous detection approaches, fluorescence lifetime detection or using optical spectrometers.

The data stream 83a may be passed on to a digital processing unit 84, to process the data to determine a positive or negative identification of faeces. The digital processing unit may perform additional functions such as detecting whether fluorescence has exceeded a preset baseline threshold to detect whether the light guide(s) are plugged in, via link 85a to sensor 85. The system may include a light source 84c and/or audible sounder 84d that light up or sound to indicate a positive identification of faeces. This sounder 84d may also be a vibration signalling device, e.g. as used on mobile phones.

The system may also include a push button or switch 84b for resetting the system to a state of negative identification i.e. where no bacteria has been detected.

Additionally, digital processing unit 84 may provide information 84a to a system control unit 86 that logs the acquired information, and provides this information to an optional data link 89 to an optional external data bus (e.g. a Universal Serial Bus, USB) through connector 89a, and/or to an optional wireless transmit-receive unit 87, such as a radio modem or other wireless transceiver that links to other devices by radiofrequency waves 87a.

The control unit 86 may include power distribution arrangements from a battery 89 and systems to charge said battery, either from the USB port or from a wireless charging arrangement 88a.

The data may include information, indicating that bacteria have been positively identified, and/or a timestamp, indicating the time when a positive identification is made. Upon positive identification, the sent data may trigger an alert on the external device(s) to be generated, such as a sound, buzzer, light, text message, or other notification to a user. Furthermore, the sent data may include status information of the detection system, such as the remaining battery capacity, and/or a 'fibre-connected/disconnected' signal (as described below).

A user may use one or more external devices to transmit to the communication module in order to configure the detection system. For example, if the external device is a smartphone or computer, a user may use a software application installed for configuration. Configuration may include identifying the patient, resetting the detection system to a state of negative identification i.e. where no bacteria has been detected. When periodic detection is performed, configuration may include selecting a time interval and duration for detection, as outlined above.

A plurality of detection systems may communicate with a single external device. For instance, a nurse or doctor could monitor the data for a plurality of patients.

Figure 9:
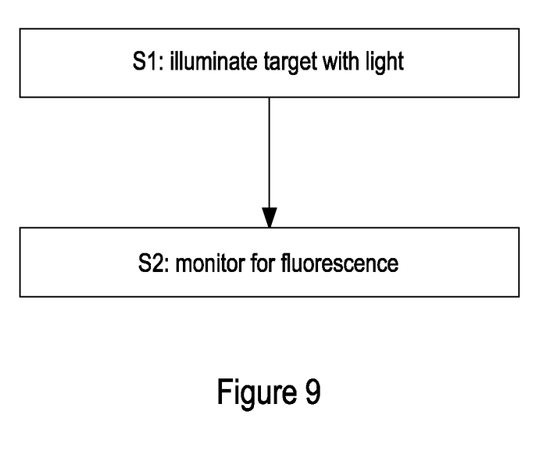
FIG. 9 illustrates a method.

FIG. 9 illustrates a method comprising a first step S1 of illuminating a target with light and a second step S2 of monitoring the target for fluorescence. Optional additional steps of this general method are described above.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

What is claimed is:

1. A method of determining the presence of human faeces using fluorescence from bacteria prevalent in human faeces, the method comprising:
    illuminating a target with excitation light having an excitation wavelength in a range of 500 nm to 645 nm; and
    monitoring for emission of fluorescence light from the target having an emission peak in a range of 675 nm to 735 nm.

2. The method of claim 1, wherein the target is illuminated with a source light guide, wherein the source light guide comprises a plurality of leaky portions along a longitudinal direction of the source light guide.

3. The method of claim 1, wherein the excitation wavelength of the excitation light has a central wavelength of substantially 635 nm.

4. The method of claim 1, wherein the excitation wavelength comprises a plurality of wavelengths corresponding to one or more porphyrin Q-bands.

5. The method of claim 1, wherein the target is a container for receiving bodily fluids or bodily excrement.

6. The method of claim 5, wherein the container is an incontinence pad, diaper or nappy, or a container for receiving a sample of bodily fluid or bodily excrement in vitro.

7. The method of claim 1, further comprising modulating intensity or frequency of the excitation light.

8. The method of claim 7, further comprising: detecting a corresponding modulation in light emitted by the target; and filtering out the emitted light without the modulation.

9. The method of claim 7, further comprising: detecting a fluorescence lifetime associated with sample fluorescence using a time-resolved or phase-resolved detection approach.

10. The method of claim 1, further comprising: providing a light source; and coupling light output from the light source into a light guide; and wherein the target is illuminated by light emitted from the light guide, and wherein the light guide comprises an optical fibre.

11. The method of claim 10, wherein the monitoring for the emission of the fluorescence light comprises monitoring for light emitted from the target into the light guide.

12. The method of claim 10, further comprising providing the light source and/or a detector in an incontinence pad, diaper or nappy.

13. The method of claim 1, further comprising:
    measuring the emission of the fluorescence light; and
    comparing the emission of the fluorescence light to a threshold value.

14. The method of claim 1, further comprising detecting a wavelength spectrum of the fluorescence light.

15. The method of claim 1, further comprising detecting a fluorescence lifetime of the fluorescence light.

16. The method of claim 1, further comprising generating a signal to notify a user of the presence of bacteria.

17. A detection system arranged to determine the presence of human faeces using fluorescence from bacteria prevalent in human faeces, comprising:
    a light source configured to emit light in a range of 500 nm to 645 nm;
    a source optical fibre, wherein the source optical fibre is optically coupled to the light source;
    a receiver optical fibre;
    a detector configured to detect light in a range of 675 nm to 735 nm, wherein the detector is optically coupled to the receiver optical fibre; and
    a signal processing unit configured to determine a positive identification of human faeces based on electronic signals, which indicate that the light, detected by the detector, has an emission peak in a range of 675 nm to 735 nm.

18. The detection system according to claim 17, wherein the source optical fibre and the receiver optical fibre are the same optical fibre, or are different optical fibres.

19. The detection system according to claim 17, wherein the source optical fibre comprises a fibre-optic cable including a core and a cladding, wherein the cladding comprises a plurality of discontinuous portions providing an optical path for light to be coupled into or out of the source optical fibre.

20. The detection system according to claim 19, wherein the discontinuous portions are arranged in a non-linear pattern in which adjacent gaps are positioned increasingly far apart from one another to maintain a constant degree of light leakage along the fibre-optic cable.

21. The detection system according to claim 17, wherein the source optical fibre and the receiver optical fibre are the same optical fibre, and wherein the optical fibre is coupled to the detector and to the light source, and wherein the detector and light source are coupled to the optical fibre at the same end of the optical fibre or at opposite ends of the optical fibre.

22. The detection system according to claim 17, further comprising a pad, wherein the source optical fibre and/or the receiver optical fibre are attached to the pad or integrally formed with the pad.

23. The detection system according to claim 17, further comprising a communication module for sending data to one or more external devices and/or receiving data from the one or more external devices.

24. The detection system according to claim 17, further comprising an alarm, wherein the alarm is one of an optical alarm, an acoustic alarm or a tactile alarm.

* * * * *